US012577566B2

(12) United States Patent
Kastrup et al.

(10) Patent No.: US 12,577,566 B2
(45) Date of Patent: Mar. 17, 2026

(54) METHODS AND COMPOSITIONS FOR MODULATING PLASMINOGEN

(71) Applicant: THE UNIVERSITY OF BRITISH COLUMBIA, Vancouver (CA)

(72) Inventors: Christian J. Kastrup, Milwaukee, WI (US); Amy W. Strilchuk, Vancouver (CA); Jerry Leung, Richmond (CA); Pieter R. Cullis, Vancouver (CA); Madelaine Robertson, Vancouver (CA)

(73) Assignee: The University of British Columbia, Vancouver (CA)

( * ) Notice: Subject to any disclaimer, the term of this patent is extended or adjusted under 35 U.S.C. 154(b) by 203 days.

(21) Appl. No.: 18/546,414

(22) PCT Filed: Feb. 14, 2022

(86) PCT No.: PCT/CA2022/050213
§ 371 (c)(1),
(2) Date: Aug. 14, 2023

(87) PCT Pub. No.: WO2022/174334
PCT Pub. Date: Aug. 25, 2022

(65) Prior Publication Data
US 2024/0141357 A1 May 2, 2024

Related U.S. Application Data

(60) Provisional application No. 63/149,720, filed on Feb. 16, 2021.

(51) Int. Cl.
| | |
|---|---|
| *C12N 15/113* | (2010.01) |
| *A61K 9/127* | (2025.01) |
| *A61K 47/14* | (2017.01) |
| *A61K 47/24* | (2006.01) |
| *A61K 47/28* | (2006.01) |
| *A61P 7/04* | (2006.01) |

(52) U.S. Cl.
CPC .......... *C12N 15/1137* (2013.01); *A61K 9/127* (2013.01); *A61K 47/14* (2013.01); *A61K 47/24* (2013.01); *A61K 47/28* (2013.01); *A61P 7/04* (2018.01); *C12N 2310/14* (2013.01)

(58) Field of Classification Search
None
See application file for complete search history.

(56) References Cited

U.S. PATENT DOCUMENTS

| | | | |
|---|---|---|---|
| 11,866,727 B2 | 1/2024 | Cowan et al. | |
| 2020/0129445 A1* | 4/2020 | Patel .................... | C12N 15/113 |

FOREIGN PATENT DOCUMENTS

| | | | | |
|---|---|---|---|---|
| CN | 111979237 A | * | 11/2020 | ................ A61P 7/04 |
| WO | 2017/077386 A1 | | 5/2017 | |

OTHER PUBLICATIONS

Extended European Search Report mailed Jun. 5, 2025, issued in corresponding Application No. EP 22 75 5443.4, filed Feb. 14, 2022, 20 pages.

International Search Report mailed May 16, 2022, issued in corresponding International Application No. PCT/CA2022/050213, filed Feb. 14, 2022, 6 pages.

Written Opinion of the International Searching Authority mailed May 16, 2022, issued in corresponding International Application No. PCT/CA2022/050213, filed Feb. 14, 2022, 7 pages.

Strilchuk, A.W. et al., "Sustained depletion of FXIII-A by inducing acquired FXIII-B deficiency," Blood, Dec. 17, 2020, vol. 136(25), pp. 2946-2954.

Supplementary Partial European Search Report mailed Feb. 21, 2025, issued in corresponding European Application No. 22 755 433.4, filed Feb. 14, 2022, 17 pages.

Nogami, K., et al., "A Novel simultaneous clot-fibrinolysis waveform analysis for assessing fibrin formation and clot lysis in haemorrhagic disorders", British Journal of Haematology, vol. 187, No. 4, Jul. 23, 2019, pp. 518-529.

Strilchuk, A.W., et al., "Lipid nanoparticles and siRNA targeting plasminogen provide lasting inhibition of fibrinolysis in mouse and dog models of hemophilia A," Science Translational Medicine, vol. 16, No. 735, Feb. 21, 2024, 9 pages.

Cheng, S-X., et al., "iTRAQ-Based Quantitative Proteomics Reveals the New Evidence Base for Traumatic Brain Injury Treated with Targeted Temperature Management," Neurotherapeutics (2018) 15:216-232.

Atkinson, J.M., et al., "An inhibitor of thrombin activated fibrinolysis inhibitor (TAFI) can reduce extracellular matrix accumulation in an in vitro model of glucose induced ECM expansion," Matrix Biology, vol. 32, No. 5, Jun. 1, 2013: 277-287.

Wittrup, A., et al., "Knocking down disease: a progress report on siRNA therapeutics," Nat Rev Genet., Sep. 2015; 16(9): 543-552.

Steinmetzer, T., et al., "Fibrinolysis Inhibitors: Potential Drugs for the Treatment and Prevention of Bleeding", Journal of Medicinal Chemistry, vol. 63, No. 4, Oct. 28, 2019, pp. 1445-1472.

(Continued)

*Primary Examiner* — Celeste A Roney

(74) *Attorney, Agent, or Firm* — Christensen O'Connor Johnson Kindness PLLC

(57) ABSTRACT

The present disclosure provides a duplex or single-stranded siRNA molecule against plasminogen, the siRNA molecule containing modified or unmodified nucleotides and wherein at least one strand of the duplex or the single-stranded siRNA has a sequence that has at least 80% sequence identity to any one of SEQ NOs: 1 to 28. Further provided is a duplex or single-stranded siRNA molecule against plasminogen, the siRNA molecule containing modified or unmodified nucleotides and is between 25 and 35 nucleotides in length. The siRNA molecule may be formulated in a lipid nanoparticle as described herein.

20 Claims, 7 Drawing Sheets

Specification includes a Sequence Listing.

(56)  References Cited

OTHER PUBLICATIONS

Kolev, K., et al., "Bleeding related to disturbed fibrinolysis," British Journal of Haematology, vol. 175, No. 1, Aug. 1, 2016, pp. 12-23.
Holmstrom, M., et al., "Combined treatment with APCC (FEIBA) and tranexamic acid in patients with haemophilia A with inhibitors and in patients with acquired haemophilia A—a two-centre experience," Haemophilia, vol. 18, No. 4, Feb. 20, 2012, pp. 544-549.

* cited by examiner

METHODS AND COMPOSITIONS FOR MODULATING PLASMINOGEN

CROSS-REFERENCES TO RELATED APPLICATIONS

This application is a National Stage of International Application No. PCT/CA2022/050213 filed Feb. 14, 2022, which claims the benefit of U.S. Provisional Patent Application Ser. No. 63/149,720 filed Feb. 16, 2021, the disclosure of each of which is expressly incorporated herein by reference in its entirety.

STATEMENT REGARDING SEQUENCE LISTING

The Sequence Listing associated with this application is provided in computer readable text format and is hereby incorporated by reference into the specification. The name of the text file containing the Sequence Listing is 1576-P10US.PNP Substitute_Sequence_Listing_PLG_ST25.txt. The text file is 16.1 KB in size; was created on 7 Dec. 2024; contains no new matter; and is being electronically submitted via Patent Center.

TECHNICAL FIELD

The present disclosure relates to nucleic acid for targeting plasminogen and pharmaceutical formulations thereof.

BACKGROUND

In bleeding disorders, patients have difficulty forming and maintaining stable clots. Bleeding disorders are caused by inherited or acquired deficiencies or defects in coagulation factors, antifibrinolytic proteins, or platelets. These include hemophilia A and B, von Willebrand Disease (VWD), platelet disorders, and other rare bleeding disorders. Severe hemophilia is typically treated with a prophylactic regimen of factor replacement therapy which involves frequent intravenous injections of the missing or defective factor. This poses high risks of thrombosis and makes patient compliance difficult. A major complication is the development of neutralizing antibodies against the infused factor that renders this therapy ineffective.

One strategy to overcome this is by using "bypassing agents" that activate the coagulation cascade downstream of the missing or deficient factor. Bypassing agents are useful for treating active episodes of bleeding, but carry risks of thrombosis and are not suitable for use as a long-term prophylactic. In contrast, "mild" hemophilia is treated on-demand, rather than prophylactically, as the risk of thrombosis is higher than bleeding. However, bleeding episodes caused by mild hemophilia are often challenging to detect, resulting in patients unaware of internal bleeding until it is too late, leading to serious damage to joints and muscles. Due to the X-linked inheritance in hemophilia A and B, the burden of these diseases on women has been greatly underestimated; severe hemophilia is rare, but up to 23% of mild hemophilia patients in treatment centres are females, and about 30% of hemophilia carriers experience abnormal bleeding. Women with bleeding disorders are often ineligible for available therapies or clinical trials as their coagulation factor levels can be too high to qualify. However, they often experience menorrhagia that severely impacts quality of life, leading to hysterectomies during the reproductive years, many of which can be avoided by properly managing bleeding with an appropriate therapy. Antifibrinolytic drugs, such as tranexamic acid (TXA), are used for short-term prophylaxis and acute bleeding in patients with a wide range of bleeding disorders. However, TXA is not suitable for long-term use due to a short activity life of only three hours. While some clinical studies have shown limited effectiveness for long-term prophylaxis, this is outweighed by mild to moderate adverse events, such as nausea and gastrointestinal distress.

Decreasing fibrinolysis long-term may be an alternate strategy to manage bleeding in a wide range of bleeding disorders. Gene therapies for bleeding are in clinical trials, but they are specific to hemophilia A or B, and none of these therapies target fibrinolysis. Gene silencing therapies using siRNA have successfully reduced the expression of anticoagulant proteins to control clotting long-term. However, clinical trials were previously halted due to fatal and non-fatal thrombotic complications, showing there are major limitations in targeting anticoagulant factors for therapeutic applications.

The present disclosure addresses one or more problems described in the prior art and/or provides useful alternatives to known approaches to treat or prevent bleeding disorders.

SUMMARY

The present disclosure in some embodiments provides a method for modifying the expression of plasminogen, thereby treating and/or preventing one or more bleeding disorders.

According to a first aspect of the disclosure, there is provided duplex or single-stranded siRNA molecule against plasminogen mRNA, the siRNA molecule containing modified or unmodified nucleotides and wherein at least one strand of the duplex or the single-stranded siRNA has a sequence that has at least 80% sequence identity to any one of SEQ ID NOs: 1 to 28.

According to a second aspect of the disclosure, there is provided duplex or single-stranded siRNA molecule against plasminogen mRNA, the siRNA molecule containing modified or unmodified nucleotides and is between 25 and 35 nucleotides in length.

In another embodiment, at least one strand of the sequence has at least 85%, 90%, 95%, 97% or sequence identity to any one of SEQ ID NOs: 1 to 28 or consists essentially of any one of such sequences.

In a further embodiment, the sequence has at least 80% sequence identity to any one of SEQ ID NOs: 1-8 or 21-28 (unmodified or modified human siRNA sequences).

In a further embodiment, the sequence is part of a conjugate molecule. In one embodiment, the conjugate molecule comprises a sugar group, including but not limited to GalNAc.

In a further embodiment, there is provided a lipid nanoparticle comprising the duplex or single-stranded siRNA molecule described in any one of the aspects of embodiments above.

In a further aspect, there is provided a lipid nanoparticle comprising: a nucleic acid for inhibiting or reducing expression of plasminogen; an ionizable, cationic lipid present at between 10 mol % and 85 mol %; a neutral vesicle-forming lipid selected from at least one of a phospholipid and a triglyceride; a sterol; and a hydrophilic polymer-lipid conjugate present at between 0.5 mol % and 5 mol %. The nucleic acid may comprise an siRNA molecule described in any one of the foregoing aspects or embodiments.

In another embodiment, there is provided a pharmaceutical composition comprising the siRNA molecule or the lipid nanoparticle described above, and wherein the pharmaceutical composition comprises a pharmaceutically acceptable salt and/or excipient.

A further embodiment includes use of the pharmaceutical composition described above to treat a bleeding disorder in a patient in need of such treatment thereof.

Another embodiment includes use of the pharmaceutical composition described above in the manufacture of a medicament to treat a bleeding disorder.

Yet further, there is provided a method of treating a patient having a bleeding disorder comprising administering the pharmaceutical composition described above to a patient in need of such treatment thereof.

In another embodiment, there is provided an siRNA for targeting mammalian plasminogen. In some embodiments, the siRNA decreases fibrinolysis and/or manages bleeding in hemophilia and other bleeding disorders.

In another embodiment the present disclosure comprises an oligonucleotide that interacts with mRNA encoding plasminogen, and results in the reduced expression of plasminogen. In one embodiment, the oligonucleotide is an siRNA. The siRNA optionally comprises a 3'-overhang and/or may be 2'-O-methylated.

In a further embodiment the present disclosure comprises an oligonucleotides of between 10-40 nucleobases in length, which comprises a contiguous nucleotide sequence of a total of between 10-40 nucleotides, and wherein the continuous nucleotide sequence is targeted to hybridize to a mammalian mRNA sequence.

In another embodiment, the present disclosure provides a method of modulating coagulation, the method comprising: administering siRNA to a subject in need thereof to inhibit the expression of plasminogen.

In another embodiment, the present disclosure comprises the use of any one or more exemplary siRNA sequences selected from SEQ ID NOs: 1-20 and duplexes thereof to inhibit the expression of plasminogen.

In another embodiment, the present disclosure provides a pharmaceutical composition comprising a siRNA in a lipid nanoparticle, wherein the siRNA inhibits expression of plasminogen.

In another embodiment the present disclosure provides an oligonucleotide that interacts with mRNA encoding plasminogen, which results in reduced expression of plasminogen as measured in vitro using western blotting and/or quantitative PCR (qPCR) as set forth in the Example section herein.

In another embodiment, the present disclosure provides a method of inhibiting expression of a coagulation factor, the method comprising: administering a pharmaceutical composition of siRNA in a lipid nanoparticle to a subject in need of inhibiting expression of plasminogen to reduce the expression of the plasminogen (siPLG/siPlg).

The siRNA optionally may comprise a 3'-overhang and/or may be 2'-O-methylated.

In a further embodiment the present invention comprises oligonucleotides of between 10-40 nucleobases in length, which comprises a contiguous nucleotide sequence of a total of between 10-40, 15-35 or 25-35 nucleotides, and wherein the continuous nucleotide sequence is targeted to hybridize to a sequence selected from the group consisting of sequences in Tables 1 and 2 (e.g., SEQ ID NOs: 1-20), or a corresponding RNA sequence in which thymine (T) is replaced with uracil (U).

Throughout this specification, unless the context requires otherwise, the words "comprise", "comprising" and the like, are to be construed in an inclusive sense as opposed to an exclusive sense, that is to say, in the sense of "including, but not limited to".

DETAILED DESCRIPTION

Figure 1:
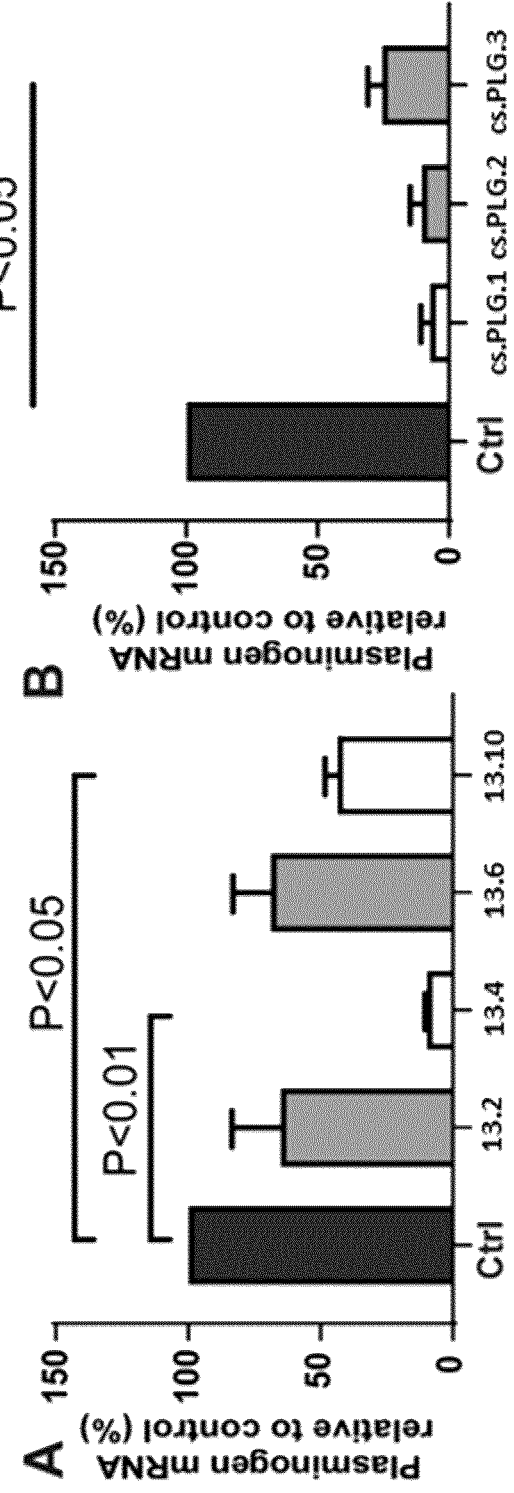
FIG. 1A shows plasminogen mRNA relative to control (%) for a luciferase siRNA control (Ctrl), and for duplex siRNA sequences, hs.Ri.PLG.13.2 (duplex siRNA of SEQ ID Nos 1 and 2), hs.Ri.PLG.13.4 (duplex siRNA of SEQ ID Nos 3 and 4), hs.Ri.PLG.13.6 (duplex siRNA of SEQ ID Nos 5 and 6) and hs.Ri.PLG.13.10 (duplex siRNA of SEQ ID Nos 7 and 8) (Table 1) after addition to HUH7 cells in vitro.
FIG. 1B shows plasminogen mRNA relative to control (%) for a luciferase siRNA control (Ctrl), and for duplex siRNA sequences, cs.PLG.1 (duplex siRNA of SEQ ID Nos 9 and 10), cs.PLG.2 (duplex siRNA of SEQ ID Nos 11 and 12) and cs.PLG.3 (duplex siRNA of SEQ ID Nos 13 and 14) siRNA after addition to canine hepatocytes in vitro.

Throughout this specification, unless the context requires otherwise, the words "comprise", "comprising" and the like, are to be construed in an inclusive sense as opposed to an exclusive sense, that is to say, in the sense of "including, but not limited to".

One embodiment of the disclosure provides siRNA sequences to reduce the expression of coagulation factors to alter clotting. In one embodiment, the coagulation factor is plasminogen. The siRNA may be a duplex siRNA. In such embodiment, the siRNA comprises a sense strand and an antisense strand, each nucleotide of the siRNA being a modified or unmodified nucleotide, and the sense and antisense strands having at least partial complementarity. In another embodiment, the siRNA is single-stranded. Further non-limiting examples of the disclosure are described in more detail hereinafter.

siRNA

The expression "siRNA molecule against plasminogen" as used herein includes a single-stranded RNA (e.g., mature miRNA) or double-stranded RNA (i.e., duplex miRNA, aiRNA, or pre-miRNA) that is capable of reducing or inhibiting the expression of plasminogen such as by mediating the degradation or inhibiting the translation of an mRNA that is complementary to the siRNA sequence as measured in vitro or in vivo. The siRNA may have substantial or complete identity to the gene that encodes plasminogen or sequence, or may comprise a region of mismatch (i.e., a mismatch motif). The sequence of the siRNA can correspond to the full-length target sequence, or a subsequence thereof.

The expression "siRNA molecule against plasminogen mRNA" as used herein includes a single-stranded RNA (e.g., mature miRNA) or double-stranded RNA (i.e., duplex RNA such as siRNA, aiRNA, or pre-miRNA) that reduces or inhibits the expression of plasminogen by mediating the degradation or inhibiting the translation of an mRNA that is complementary to the siRNA sequence as measured in vitro or in vivo.

In some embodiments, the siRNA is 15 to 40 or 20 to 35 nucleotides in length. In another embodiment, the siRNA is at least 25 nucleotides in length, for example, 25 to 40 nucleotides in length or 25 to 35 nucleotides in length, or any range therebetween. If the siRNA is double-stranded, then the nucleotide length corresponds to the length of an antisense or sense strand.

The siRNA described herein may comprise a "mismatch motif" or "mismatch region", which refers to a portion of the siRNA sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

In some embodiments, the siRNA inhibits expression of plasminogen as measured in vitro or in vivo. Inhibition or reduction of expression of a target gene or target sequence is achieved when the value obtained with an interfering RNA relative to a relevant control is about 90%, 85%, 80%, 75%, 70%, 65%, 60%, 55%, 50%, 45%, 40%, 35%, 30%, 25%, 20%, 15%, 10%, 5% or 0%. Suitable assays for measuring expression of a target gene or target sequence include, e.g., examination of protein or RNA levels using techniques known to those of skill in the art such as quantitative PCR (qPCR), western blots, dot blots, northern blots, in situ hybridization, ELISA, immunoprecipitation, enzyme function, as well as phenotypic assays known to those of skill in the art. The reduction in expression in vitro may be measured using an assay as described in the Example section. Phenotypic assays include clotting or other assays in model organisms as described herein in the Example section to assess treatment or prevention of a bleeding disorder.

The expression "inhibiting or reducing expression of plasminogen", includes inhibition or reduction of plasminogen expression that is achieved when the value obtained with an interfering RNA relative to a relevant control is about 90%, 85%, 80%, 75%, 70%, 65%, 60%, 55%, 50%, 45%, 40%, 35%, 30%, 25%, 20%, 15%, 10%, 5% or 0% using any one of the assays set forth above. Either mRNA or protein levels may be assayed in certain embodiments.

The nucleotides of the siRNA may be modified. Examples of modifications include, but are not limited to, 2'-O-alkyl modifications such as 2'-O-Me modifications and 2'-halogen modifications such as 2'-fluoro modifications.

The siRNA may have sequence identity to any one of the nucleotide sequences set forth in Table 1, Table 2 and Table 3 below. The expression "sequence identity" when referring to two nucleic acids herein, refers to two sequences or subsequences that are the same or have a specified percentage of nucleotides that are the same, when compared and aligned for maximum correspondence over a comparison window, or designated region as measured using a known comparison algorithm or by manual alignment and visual inspection.

For determining sequence identity, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. The sequence identity is typically measured by BLAST, which is well-known to those of skill in the art.

In one embodiment, the siRNA has at least 30% to 100% sequence identity to any one of SEQ ID NOs: 1-28 in Table 1, Table 2 and Table 3 below. For example, the siRNA may have at least 40%, at least 50%, at least 55%, at least 60%, at least 65%, at least 70%, at least 75%, at least 80%, at least 85%, at least 90%, at least 95%, at least 98% sequence identity to any one of SEQ ID Nos: 1-28. In one embodiment, a strand of the siRNA consists essentially of any one of SEQ ID NOs: 1-28 meaning that the strand differs by no more than 4 nucleotides but excluding modifications of the nucleotides, such as methylation or a halogen modification (described below).

In a further embodiment, the siRNA or a strand of a duplex siRNA differs by no more than 1, 2, 3, 4, 5, 7, 8, 9, 10, 11, 12, 13, 14 or 15 nucleotides as set forth in SEQ ID NOs: 1-28. In one embodiment, the siRNA differs by no more than 10 nucleotides or no more than 5 nucleotides. In in one embodiment, this excludes differences due to modifications of a given nucleotide, such as methylation or a halogen modification (described below).

In another embodiment the present disclosure provides one or more exemplary siRNA sequences or duplexes thereof selected from SEQ ID NOs: 1-8 or SEQ ID NOs: 21-28 (human sequences) to inhibit or reduce the expression of plasminogen.

In one embodiment, the siRNA has at least 30% to 100% sequence identity to any one of SEQ ID NOs: 1-8 in Table 1 or SEQ ID NOs 21-28 in Table 3 below. For example, the siRNA may have at least 40%, at least 50%, at least 55%, at least 60%, at least 65%, at least 70%, at least 75%, at least 80%, at least 85%, at least 90%, at least 95%, at least 98% sequence identity to any one of SEQ ID Nos: 1-8 in Table 1 or SEQ ID NOs 21-28 in Table 3 below. In one embodiment, the siRNA consists essentially of any one of SEQ ID NOs: 1-8 in Table 1 or SEQ ID NOs: 21-28 in Table 3 below, meaning that it differs by no more than 4 nucleotides excluding modifications of the nucleotides, such as methylation or a halogen modification (described below).

It should be appreciated that the sequence identity herein need not require an exact match of two nucleotides. To illustrate, a given nucleotide can be methylated and will be considered to have identity to an unmethylated nucleotide.

In a further embodiment, the siRNA or a strand of a duplex siRNA differs by no more than 1, 2, 3, 4, 5, 7, 8, 9, 10, 11, 12, 13, 14 or 15 nucleotides as set forth in SEQ ID NOs: 1-8 in Table 1 and SEQ ID NOs: 21-28 in Table 3 below. In one embodiment, the siRNA differs by no more than 10 nucleotides or no more than 8, 7, 6 or 5 nucleotides from the sequences in Table 1 and Table 3 below. In in one embodiment, this excludes differences due to modifications of a given nucleotide, such as methylation or a halogen modification (described below).

In another embodiment the present disclosure provides one or more siRNA sequences or duplexes thereof selected from SEQ ID NOs: 1-8 (Table 1) and SEQ ID NOs: 21-28 (Table 3) to inhibit or reduce the expression of plasminogen.

In another embodiment, the present disclosure provides one or more siRNA sequences or duplexes thereof selected from SEQ ID NOs: 1-8 (Table 1) to inhibit or reduce the expression of plasminogen and the siRNA or a strand of a duplex siRNA differs by no more than 1, 2, 3, 4, 5, 7, 8, 9, 10, 11, 12, 13, 14 or 15 nucleotides and/or 0 to 50% or 10 to 40% of the nucleotides have 2'-O-alkyl modifications such as 2'-O-Me modifications and/or 2'-halogen modifications.

Without being limiting, the siRNA sequences may exhibit a modification pattern similar to that set forth in Table 2 or Table 3 below.

TABLE 1

| Base composition of duplex siRNA sequence targeting human plasminogen mRNA | | |
|---|---|---|
| Sequence Name | SEQ ID NO. | Base composition of the duplex siRNA targeting human Plasminogen mRNA |
| hs.Ri.PLG.13.2 | 1 | 5'-CAAGAAGUUGUCCACGCAUUUAC CU-3' |
| | 2 | 5'-AGGUAAAUGCGUGGACAACUUCU UGGC-3' |
| hs.Ri.PLG.13.4 | 3 | 5'-CGCUCAUGGAUACAUUCCUUCCA AA-3' |
| | 4 | 5'-UUUGGAAGGAAUGUAUCCAUGAG CGU-3' |
| hs.Ri.PLG.13.6 | 5 | 5'-GUAAGCAUAUCAGGUUAGAACUC UC-3' |
| | 6 | 5'-GAGAGUUCUAACCUGAUAUGCUU ACUU-3' |
| hs.Ri.PLG.13.10 | 7 | 5'-UGCAAUCGCUAUGAGUUUCUGAA UG-3' |
| | 8 | 5'-CAUUCAGAAACUCAUAGCGAUUG CACA-3' |

TABLE 2

| Base modification of duplex siRNA sequences targeting murine or canine plasminogen mRNA. "r" designates unmodified base, "m" designates 2'O-methylated base | | |
|---|---|---|
| Sequence Name | SEQ ID NO | Base composition of the duplex siRNA targeting murine or canine plasminogen mRNA (5'-3') |
| cs.PLG.1 | 9 | rUrCmUrUrUrArCrUmGrUmGrAmUrArUrUrGrGrArArUrGmArCmCmUmG |
| | 10 | mGmGrUmCrAmUrUrCrCrArAmUrAmUrCmArCmArGrUrArArAmGrA |

TABLE 2-continued

Base modification of duplex siRNA sequences targeting murine or
canine plasminogen mRNA. "r" designates unmodified
base, "m" designates 2'O-methylated base

| Sequence Name | SEQ ID NO | Base composition of the duplex siRNA targeting murine or canine plasminogen mRNA (5'-3') |
|---|---|---|
| cs.PLG.2 | 11 | rGrUmArArUrUrCrAmUrCmUrUmCrArArGrUrUrCrUrUrGmCrUmUmGmG |
| | 12 | mAmArGmCrAmArGrArArCrUmUrGmArAmGrAmUrGrArArUrUmArC |
| cs.PLG.3 | 13 | rCrUmCrUrUrUrArCmUrGmUrGmArUrArUrUrGrGrArArUmGrAmCmCmU |
| | 14 | mGmUrCmArUmUrCrCrArArUmArUmCrAmCrAmGrUrArArArGmArG |
| ms.PLG.1 | 15 | rArAmGrCrUrUrUrAmGrUmArAmGrCrArGrArGrGrUrUrUmUrGmCmUmC |
| | 16 | mGmCrAmArAmArCrCrUrCrUmGrCmUrUmArCmUrArArArGrCmUrT |
| ms.PLG.2 | 17 | rUrCmUrUrCrArCrAmUrUmCrAmGrGrArArUrGrUrUrGrCmArGmUmAmG |
| | 18 | mAmCrUmGrCmArArCrArUrUmCrCmUrGmArAmUrGrUrGrArAmGrA |
| ms.PLG.3 | 19 | rArGmGrArUrArArCmCrUmUrGmUrArGrArArUrUrCrArGmGrUmCmUmU |
| | 20 | mGmArCmCrUmGrArArUrUrCmUrAmCrAmArGmGrUrUrArUrCmCrT |

TABLE 3

Human siRNA sequences with modifications

| Sequence Name | SEQ ID NO | Base composition of the duplex siRNA targeting human Plasminogen mRNA (5'-3') |
|---|---|---|
| hs.Ri.PLG.13.2 | 21 | mCmArAmGrAmArGrUrUrGrUmCrCmArCmGrCmArUrUrUrArCmCrT |
| | 22 | rArGmGrUrArArArUmGrCmGrUmGrGrArCrArArCrUrUrCmUrUmGmGmC |
| hs.Ri.PLG.13.4 | 23 | mCmGrCmUrCmArUrGrGrArUmArCmArUmUrCmCrUrUrCrCrAmArA |
| | 24 | rUrUmUrGrGrArArGmGrAmArUmGrUrArUrCrCrArUrGrAmGrCmGmU |
| hs.Ri.PLG.13.6 | 25 | mGmUrAmArGmCrArUrArUrCmArGmGrUmUrAmGrArArCrUrCmUrC |
| | 26 | rGrAmGrArGrUrUrCmUrAmArCmCrUrGrArUrArUrGrCrUmUrAmCmUmU |
| hs.Ri.PLG.13.10 | 27 | mUmGrCmArAmUrCrGrCrUrAmUrGmArGmUrUmUrCrUrGrArAmUrG |
| | 28 | rCrAmUrUrCrArGrAmArAmCrUmCrArUrArGrCrGrArUrUmGrCmAmCmA |

It should be appreciated that an siRNA having a sequence similar to those set forth in the sequence listings may optionally be conjugated with another moiety, such as but not limited to a ligand, as described below.

Within an siRNA, the antisense strand and the sense strand may be designed such that when they form a duplex due to complementarity of base-pairs, they can anneal with no overhangs and thus form blunt ends at both ends of the duplex, or with an overhang at one or more of the 3' end of the sense strand, the 3' end the antisense strand, the 5' end of the sense strand, and the 5' end of the antisense strand. In some embodiments, there are no 5' overhangs and there is no 3' antisense overhang, but there is a 3' sense overhang. In other aspects, there are no 5' overhangs, but there are a 3' antisense overhang and a 3' sense overhang.

When overhangs are present, they may, for example, be 1 to 6 nucleotides long. In some aspects, the overhang is a dinucleotide. By way of a non-limiting example, in one aspect, there is a 3' sense overhang that is dTdT, and there are no overhangs on the antisense strand and no 5' sense overhang. By way of another non-limiting example, in another aspect, there are a 3' sense overhang that is dTdT and a 3' antisense overhang that also is dTdT, but there are no 5' overhangs on either the antisense strand or the sense strand. By way of another non-limiting example, in one aspect, there is a 3' sense overhang that is dTdT, and a 3' dinucleotide antisense overhang that is complementary to two nucleotides on the target molecule adjacent to the region of the target molecule to which the region of the antisense strand within the duplex is complementary. In this aspect, there are no 5' overhangs on either the antisense strand or the sense strand. When an overhang is present, the nucleotides within it are included in the aforementioned range of 18 to 30 nucleotides for each strand.

In some aspects, the siRNA are covalently bound to one or more other molecules to form a conjugate. In some aspects, the conjugates are selected because they facilitate delivery of the siRNA to an organism or into cells. An siRNA may be bound to a conjugate at, for example, the 5' end of the antisense strand, the 3' end of the antisense strand, the 5' end of the sense strand, the 3' end of the sense strand, or to a nucleotide at a position that is not at the 3' end or 5' end of either strand.

Examples of conjugates include but are not limited to one or more of an antibody, a peptide, an amino acid, an aptamer, a phosphate group, a cholesterol moiety, a lipid, a cell-penetrating peptide polymer, and a sugar group, which includes a sugar monomer, an oligosaccharide and modifications thereof. In one aspect, the conjugate is N-Acetylga-lactosamine (GalNAc).

Lipid Nanoparticles

In one embodiment, the disclosure provides a nucleic acid against plasminogen mRNA that is encapsulated within a lipid nanoparticle. In one embodiment, the nucleic acid is for inhibiting or reducing expression of plasminogen.

It will be understood that the invention is not limited by the location or the nature of the incorporation of the nucleic acid within the lipid nanoparticle. That is, the term "encapsulated" is not meant to be limited to any specific interaction between the nucleic acid and the lipid nanoparticle. The nucleic acid may be incorporated in the aqueous portion, within any lipid layer or both.

The lipid nanoparticle (LNP) described herein may comprise an ionizable lipid that may associate or complex with the nucleic acid. The term "ionizable lipid" refers to any of a number of lipid species that carry a net positive charge at a selected pH below its pKa. In some embodiments, the cationic lipid has a head group comprising an amino group. In some embodiments, the cationic lipids comprise a protonatable tertiary amine (e.g., pH titratable) head group, C16 to C18 alkyl chains, ether linkages between the head group and alkyl chains, and 0 to 3 double bonds.

In certain embodiments, the cationic lipid content is from 20 mol % to 70 mol % or 30 mol % to 55 mol % or 35 mol % to 55 mol % of total lipid present in the lipid nanoparticle.

The lipid nanoparticle (LNP) described herein may comprise a helper lipid in addition to the ionizable lipid. In the context of the present disclosure, the term "helper lipid" includes any vesicle-forming lipid (e.g., bilayer-forming lipid) that may be selected from a phosphatidylcholine lipid, sphingomyelin, or mixtures thereof. In some embodiments, the helper lipid is selected from sphingomyelin, distearoylphosphatidylcholine (DSPC), dioleoylphosphatidylcholine (DOPC), 1-palmitoyl-2-oleoyl-phosphatidylcholine (POPC) and dipalmitoyl-phosphatidylcholine (DPPC). In certain embodiments, the helper lipid is DOPC, DSPC or sphingomyelin. In one embodiment, the helper lipid is DSPC. The helper lipid content may include mixtures of two or more different types of different helper lipids.

For example, in certain embodiments, the phosphatidylcholine content is from 20 mol % to 60 mol % or 25 mol % to 60 mol % or 30 mol % to 60 mol % or 35 mol % to 60 mol % or 40 mol % to 60 mol % of total lipid present in the lipid nanoparticle. The phosphatidylcholine lipid content is determined based on the total amount of lipid in the lipid nanoparticle, including the sterol.

In one embodiment, the LNP comprises a sterol, a hydrophilic polymer-lipid conjugate or both. Examples of sterols include cholesterol, or a cholesterol derivative, such as cholestanol, cholestanone, cholestenone, coprostanol, cholesteryl-2'-hydroxyethyl ether, cholesteryl-4'-hydroxybutyl ether, beta-sitosterol, fucosterol and the like. In one embodiment, the sterol is present at from 15 mol % to 65 mol %, 18 mol % to 50 mol %, 20 mol % to 50 mol %, 25 mol % to 50 mol % or 30 mol % to 50 mol % based on the total lipid present in the lipid nanoparticle. In another embodiment, the sterol is cholesterol and is present at from 15 mol % to 65 mol %, 18 mol % to 50 mol %, 20 mol % to 50 mol %, 25 mol % to 50 mol % or 30 mol % to 50 mol % based on the total lipid and sterol present in the lipid nanoparticle.

In one embodiment, the hydrophilic-polymer lipid conjugate includes (i) a vesicle-forming lipid having a polar head group, and (ii) covalently attached to the head group, a polymer chain that is hydrophilic. Example of hydrophilic polymers include polyethyleneglycol (PEG), polyvinylpyrrolidone, polyvinylmethylether, polyhydroxypropyl methacrylate, polyhydroxypropylmethacrylamide, polyhyd.-oxyethyl acrylate, polymethacrylamide, polydimethylacrylamide, polymethyloxazoline, polyethyloxazoline, polyhydroxyethyloxazoline, polyhydroxypropyloxazoline, polysarcosine and polyaspartamide. In one embodiment, the hydrophilic-polymer lipid conjugate is a PEG-lipid conjugate.

The hydrophilic polymer lipid conjugate may be present in the nanoparticle at 0 mol % to 5 mol %, or at 0.5 mol % to 3 mol %, or at 0.5 mol % to 2.5 mol % or at 0.5 mol % to 2.0 mol % or at 0.5 mol % to 1.8 mol % of total lipid. In another embodiment, the PEG-lipid conjugate is present in the nanoparticle at 0 mol % to 5 mol %, or at 0.5 mol % to 3 mol % or at 0.5 mol % to 2.5 mol % or at 0.5 mol % to 2.0 mol % or at 0.5 mol % to 1.8 mol % of total lipid. In certain embodiments, the PEG-lipid conjugate may be present in the nanoparticle at 0 mol % to 5 mol %, or at 0 mol % to 3 mol %, or at 0 mol % to 2.5 mol % or at 0 mol % to 2.0 mol % or at 0 mol % to 1.8 mol % of total lipid.

Methods to Treat or Prevent Bleeding Disorders

In another aspect, the present disclosure provides methods of treating a subject having any disorder or condition that would benefit from reduction in plasminogen expression.

This includes a "bleeding disorder", which as used herein includes any condition, of any severity, that results in abnormal amounts of bleeding in a subject, such as but not limited to a blood clotting disorder. The bleeding disorder includes but is not limited to hemophilia A and B, von Willebrand Disease (VWD), platelet disorders, menorrhagia and other rare bleeding disorders or conditions. The methods include administering to the subject a therapeutically effective amount of the siRNA, optionally encapsulated in a lipid nanoparticle, thereby treating the subject or providing a prophylactic effect.

As used herein, the term "subject" includes any human or non-human mammalian subject that would benefit from a reduction in plasminogen expression relative to lack of treatment thereof. This includes a prophylactic benefit in some embodiments.

In one embodiment, the disclosure provides methods of preventing at least one symptom, e.g., bleeding, in a subject having a bleeding disorder that would benefit from reduction in plasminogen expression. The methods include administering to the subject a therapeutically effective amount of the siRNA, e.g., duplex RNA, or vector thereof, thereby preventing at least one symptom in the subject having a disorder that would benefit from reduction in plasminogen expression.

In one embodiment, the administration of the dsRNA to the subject causes an increase in blood clotting and/or a decrease in plasminogen protein expression and/or accumulation.

In another embodiment the present disclosure provides a method of treating a patient by modulating coagulation, the method comprising: administering siRNA to a subject in need thereof to inhibit the expression of plasminogen. Modulation of coagulation or clotting can be assessed as set forth in the Example section herein.

Further methods for assessing knockdown, inhibition and/or reduction in plasminogen expression include thromboelastography (TEG), a clot stiffness assay, a clot lysis assay and/or quantifying plasma plasminogen protein concentration. Inhibition of expression of a target gene or target sequence is achieved when the value obtained with an siRNA relative to a relevant control is about 90%, 85%, 80%, 75%, 70%, 65%, 60%, 55%, 50%, 45%, 40%, 35%, 30%, 25%, 20%, 15%, 10%, 5%, or 0%.

In another embodiment, the siRNA is used to treat a cell in vitro or in vivo. The cell may be within a subject, such as a mammalian subject, for example a human subject suffering from a bleeding disorder. One embodiment of the disclosure provides a method to knock-down plasminogen using siRNA delivered to hepatocytes.

Pharmaceutical Formulations

In some embodiments, the siRNA or lipid nanoparticle comprising a nucleic acid reducing expression plasminogen is part of a pharmaceutical composition and is administered to treat and/or prevent a disease condition. The treatment may provide a prophylactic (preventive), ameliorative or a therapeutic benefit to treat a bleeding disorder. The pharmaceutical composition will be administered at any suitable dosage.

In one embodiment, the pharmaceutical composition is administered parenterally, i.e., intra-arterially, intravenously, subcutaneously or intramuscularly. In another embodiment, the pharmaceutical compositions are administered intranasally, intravitreally, subretinally, intrathecally or via other local routes.

The pharmaceutical composition comprises pharmaceutically acceptable salts and/or excipients. Used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

As used herein, the term "excipient" means the substances used to formulate active pharmaceutical ingredients (API) into pharmaceutical formulations. Non-limiting examples include mannitol, Captisol®, lactose, starch, magnesium stearate, sodium saccharine, talcum, cellulose, sodium crosscarmellose, glucose, gelatin, sucrose, magnesium carbonate, and the like. Acceptable excipients are non-toxic and may be any solid, liquid, semi-solid excipient that is generally available to one of skill in the art.

The examples are intended to illustrate preparations and properties of the invention but are in no way intended to limit the scope of the invention.

EXAMPLES

Materials and Methods siRNA-LNP Preparation, Analysis, and Administration

2'O-methylated siRNA, obtained commercially (Integrated DNA Technologies, Coralville, IW) was dissolved in 25 mM sodium acetate pH 4 buffer at an amine-to-phosphate (N/P) ratio of 3. Ionizable cationic lipid, DSPC, cholesterol and PEG-DMG, were dissolved in ethanol at a molar ratio of 50/10/38.5/1.5 mol %, respectively, to achieve a final concentration of 20 mM total lipid. The two solutions were mixed using a T-junction mixer as described previously. The resulting lipid nanoparticles were dialyzed against phosphate buffered saline (PBS) pH 7.4 in a 1000-fold excess. Cholesterol content was measured using a Cholesterol E Assay Kit (Wako Chemicals, Mountain View, CA), from which total lipid concentration was extrapolated. Nucleic acid entrapment was determined using a RiboGreen assay. siRNA-LNPs were administered to mice and dogs intravenously. siRNA targeting plasminogen (siPLG) was used as treatment, and PBS or siRNA targeting luciferase (siLuc) were used as a control.

Murine Blood Draws

Murine studies were performed in accordance with the University of British Columbia and University of Cincinnati Animal Care Committee approved protocols. C57BL/6J, and B6; 129S-F8tm1Kaz/J, (Jackson Labs, Bar Harbor, ME, stock #000664, #101045, #004424) mice were utilized in all studies. Blood samples used to assess plasma protein level were collected via saphenous vein puncture (C57BL/6J mice) into heparinized capillaries via a 25G needle. Blood was drawn for coagulation assays from isoflurane anesthetized mice by cardiac puncture using a 23G needle containing sodium citrate (109 mM) to a final v/v concentration of 10% in whole blood. To collect plasma, whole blood spun at 800×g for 10 minutes.

mRNA Quantification

Cells were collected from culture plates, or liver tissue was surgically removed from anesthetized mice and was homogenized in Trizol (ThermoFisher, Waltham, MA). Nucleic acid was extracted by phenol-chloroform precipitation. DNA was digested by incubating the sample with TURBO DNase (ThermoFisher) at 37° C. for 1 hour. DNase was removed by repeating the Trizol-chloroform extraction. Reverse transcription was performed using the iScript cDNA Synthesis Kit (Bio-Rad, Hercules, CA) followed by qPCR with SYBR Green Master Mix (ThermoFisher) and DNA primers (IDT, Coralville, IA).

Western Blotting

Samples were reduced, boiled, and separated on 4-15% acrylamide gradient gels (Bio-Rad). After electrophoresis, the samples were transferred to a nitrocellulose membrane (GE Healthcare, Chicago, IL) and blocked with Odyssey Blocking Buffer (LI-COR, Lincoln, NE). The membranes were treated with a primary antibody against plasminogen (1:1000; confirmed cross-reactivity: human, rat, mouse, rabbit, canine; Affinity Biologicals, Ancaster, ON, Canada), washed, and treated with HRP-labeled anti-host secondary antibody (1:15,000; Abcam, Cambridge, MA). Specific bands were imaged using Clarity ECL (Bio-Rad) on film (Mandel, Guelph, ON, Canada). Quantification of western blots was done using ImageJ (NIH, Bethesda, MD) to measure band intensity relative to background and loading controls.

Thromboelastography (TEG)

Shear elastic moduli were evaluated at 37° C. using a TEG Hemostasis Analyzer System 5000 (Haemoscope Corp., Niles, IL). Citrated mouse whole blood or canine plasma was combined with $CaCl_2$ (10 mM), thrombin (0.03 nM Innovin, MedCorp, Brazil), and tissue plasminogen activator (tPA; 3.8 nM) over 3 h.

Saphenous Vein Puncture Bleeding Model

Two weeks after siPLG administration, mice were anesthetized with 10-15% isoflurane, and kept on a heating pad. After fur removal, vein was visualized under 10× magnification stereoscope. Vein was isolated from artery and nerve; after a rest period of approximately 5 minutes, a puncture wound was made using the bevel of a 26-gauge needle. Blood was collected on pre-weighed filter paper. Blood loss was measured by weight of paper after blood absorption.

Statistical Analysis

Statistical analyses were performed using GraphPad Prism 8.0.1. All results presented in graphs are the mean±SEM. N indicates number of biological replicates. For groups of sufficient size (N≥3), significance was assessed. Two-tailed unpaired Student's t test was used to compare two data sets. Two-way ANOVA was used to compare two data sets over time, one-way ANOVA was used to compare multiple data sets with one variable. Welch's ANOVA was used when variance was not equal (Brown- Forsythe), all data was of normal distribution (Shapiro-Wilk). Significance was designated at P values<0.05.

Example 1: siRNA Knock Down In Vitro

This example demonstrates that siRNA knocks down plasminogen in human and canine hepatocytes in vitro.

Quantitative PCR as described in the Materials and Methods was used to measure plasminogen mRNA after administration of different siRNA sequences targeting plasminogen to human (FIG. 1A), or canine (FIG. 1B) hepatocytes cells in culture.

As shown in FIG. 1A, significant depletion of plasminogen mRNA was observed in vitro after treatment with select siRNA sequences set out in Table 1, namely hs.Ri.PLG.13.2 (SEQ ID Nos 1 and 2), hs.Ri.PLG.13.4 (SEQ ID Nos 3 and 4), hs.Ri.PLG.13.6 (SEQ ID Nos 5 and 6) and hs.Ri.PLG.13.10 (SEQ ID Nos 7 and 8), compared to negative control (black) in human HUH7 cells.

Similarly, in canine hepatocytes, significant depletion of plasminogen mRNA was observed with sequences of Table 2. As can be seen in FIG. 1B, the sequences cs.PLG.1 (SEQ ID Nos 9 and 10), cs.PLG.2 (SEQ ID Nos 11 and 12) and cs.PLG.3 (SEQ ID Nos 13 and 14) siRNA displayed depletion of plasminogen mRNA relative to the control.

Example 2: siRNA Knock Down of Plasminogen In Vivo and Clot Stability

This example shows that siRNA knocks down plasminogen in mice and makes clots more stable ex vivo in fibrinolytic conditions.

PCR (qPCR) as described in the Materials and Methods was used to quantify hepatic plasminogen mRNA after administration of three different murine siRNA sequences targeting plasminogen to mice 3 days prior to tissue collection compared to control siRNA targeting luciferase (siLuc).

Figure 2:
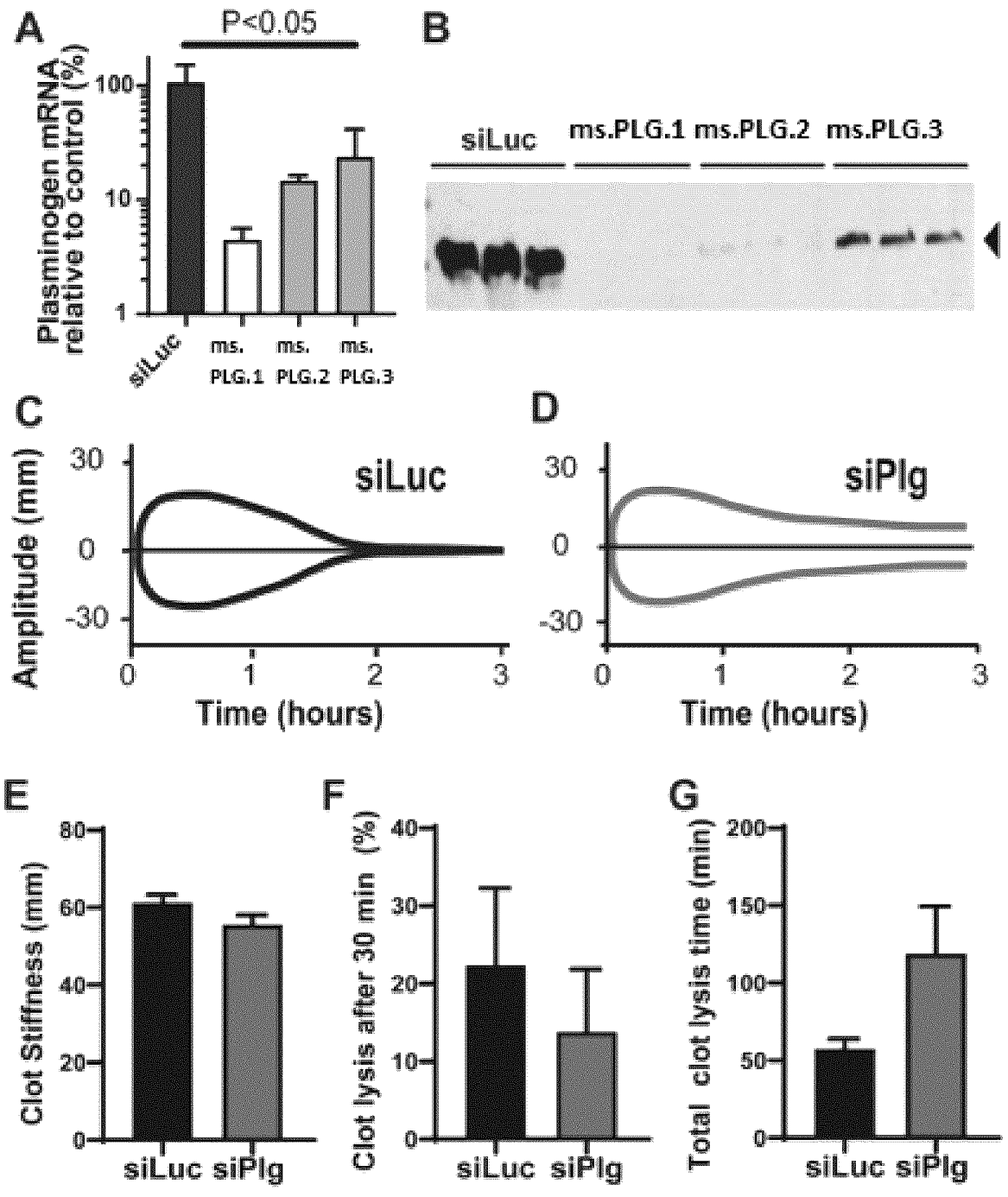
FIG. 2A shows plasminogen mRNA relative to control for duplex siRNA against luciferase (siLuc) and ms.PLG.1 (duplex siRNA of SEQ ID Nos 15 and 16), ms.PLG.2 (duplex siRNA of SEQ ID Nos 17 and 18) and ms.PLG.3 (duplex siRNA of SEQ ID Nos 19 and 20) in the liver tissue of mice.
FIG. 2B is a western blot detecting plasminogen in plasma 3 days after injection to mice of control LNP siluciferase (siLuc) and LNP siRNA targeting plasminogen (siPlg), namely duplex siRNA against luciferase (siLuc) and ms.PLG.1 (SEQ ID Nos 15 and 16), ms.PLG.2 (SEQ ID Nos 17 and 18) and ms.PLG.3 (SEQ ID Nos 19 and 20).
FIG. 2C shows results of thromboelastography (TEG) in amplitude (mm) vs time (hours) to measure clot properties ex vivo in blood from mice treated with siRNA against luciferase (siLuc), in profibrinolytic conditions.
FIG. 2D results of thromboelastography (TEG) in amplitude (mm) vs time (hours) to measure clot properties ex vivo in blood from mice treated with siPlg corresponding to ms.PLG.1 (SEQ ID Nos 15 and 16) of Table 2 (right bar).
FIG. 2E shows clot stiffness (mm) after treatment of mice with siRNA against luciferase (siLuc) (control; left bar) and siPlg corresponding to ms.PLG.1 (SEQ ID Nos 15 and 16) of Table 2 (right bar).
FIG. 2F shows clot lysis after 30 minutes (%) after treatment of mice with siRNA against luciferase (siLuc) (control; left bar) and siPlg corresponding to ms.PLG.1 (SEQ ID Nos 15 and 16) of Table 2 (right bar).
FIG. 2G shows total clot lysis time (minutes) after treatment of mice with siRNA against luciferase (siLuc) (control; left bar) and siPlg corresponding to ms.PLG.1 (SEQ ID Nos 15 and 16) of Table 2 (right bar).

The results are shown in FIG. 2A. As can be seen in FIG. 2A, plasminogen mRNA relative to control (siLuc) was significantly reduced in the liver tissue of mice after administration of the following siRNA sequences: ms.PLG.1 (SEQ ID Nos 15 and 16), ms.PLG.2 (SEQ ID Nos 17 and 18) and ms.PLG.3 (SEQ ID Nos 19 and 20) of Table 2.

The protein levels of plasminogen were also assessed in mice after administration of the above siRNA sequences and control luciferase. Plasminogen protein levels were assessed by western blot in plasma collected from mice 3 days after treatment. The results are shown in FIG. 2B, which shows that the control (siLuc) treatment had high levels of plasminogen, while treatment with the murine siRNA sequences show significant reduction in plasminogen protein concentration (right arrow).

Thromboelastography (TEG) as described in the Materials and Methods was used to measure clot properties ex vivo in blood from mice treated with ms.PLG.1 (SEQ ID Nos 15 and 16) (grey) or siLuc (black), in profibrinolytic conditions. The results are shown in FIGS. 2C (siLuc control) and FIG. 2D (siPlg=ms.PLG.1).

Clot stiffness and clot lysis were investigated using the procedures set forth in the Materials and Methods for ms.PLG.1 (SEQ ID Nos 15 and 16). Clot stiffness results are shown in FIG. 2E, and propensity for clot lysis are shown in FIG. 2F and FIG. 2G.

The results of FIG. 2E show that siRNA siPlg knocks down plasminogen in mice, and makes clots more stable ex vivo in fibrinolytic conditions relative to the siLuc control. FIG. 2F shows clot lysis after 30 minutes (%) was reduced for siPlg relative to the siLuc control. Similarly, FIG. 2G shows total clot lysis time (min) was extended for siPlg relative to siLuc.

Example 3: Long Term Knockdown of Plasminogen In Vivo

This example shows long term knockdown can be achieved with siRNA, with no observed toxicity, in mice.

Mice were administered with siPlg siRNA (siPlg=ms.PLG.1 duplex siRNA of Table 2) or siLuc control. The plasma concentration of plasminogen was assayed at various points after administration. In addition, the mouse weight was determined at various points post-injection to assess toxicity.

Figure 3:
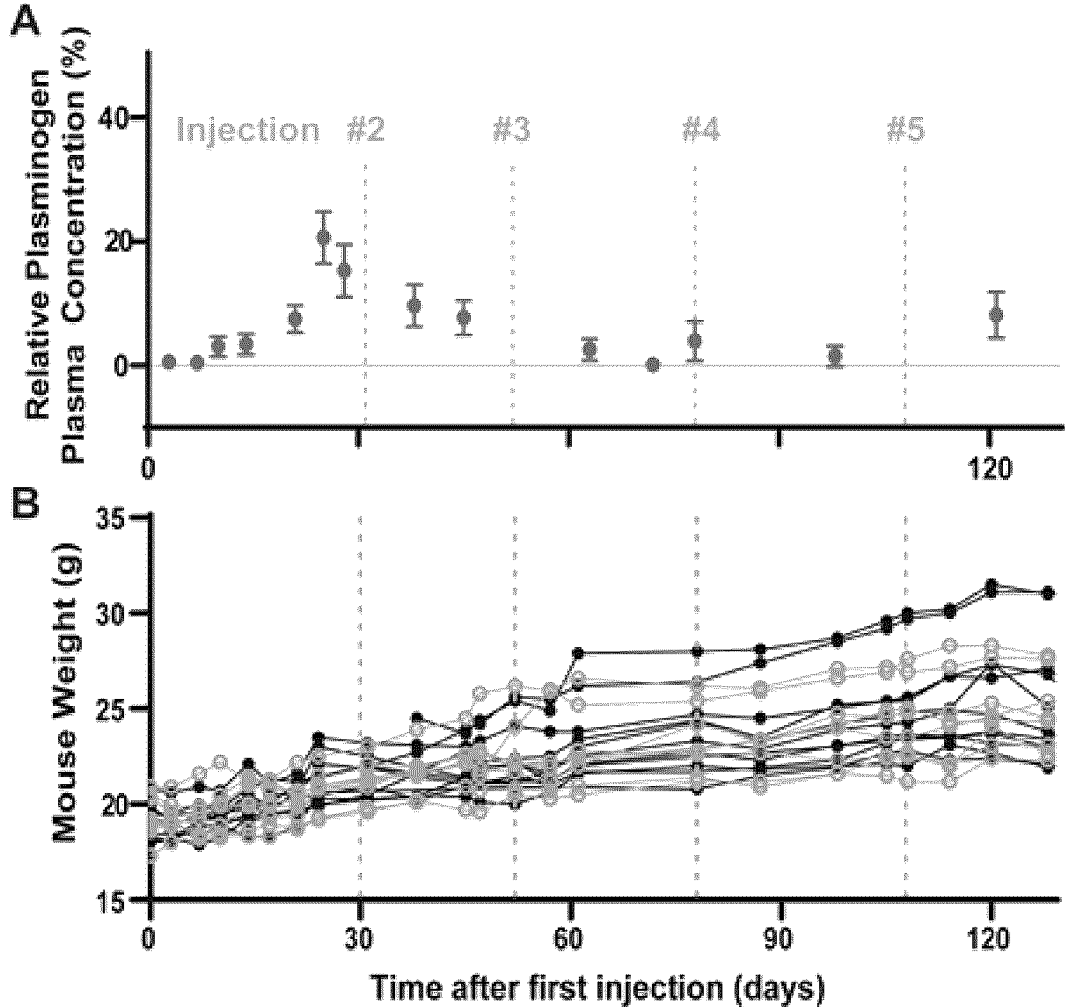
FIG. 3A shows plasminogen protein levels in plasma after administration of siPlg at 3-4 week intervals (corresponding to ms.PLG.1 (SEQ ID Nos 15 and 16) of Table 2).
FIG. 3B shows mouse weight over the course of prolonged knockdown in mice treated with siPlg corresponding to ms.PLG.1 (SEQ ID Nos 15 and 16) of Table 2 (filled symbols) and siLuc control (open symbols).

As shown in FIG. 3A, plasminogen protein level in plasma shows that the knockdown lasts for 3 weeks after a single administration of siPlasminogen and can be prolonged indefinitely with regular administrations at 3-week intervals. As shown in FIG. 3B, weight gain over the course of prolonged knockdown shows no difference between mice treated with siPlg (filled symbols) and siLuc (open symbols).

Example 4: Knockdown of Plasminogen does not Cause Plasminogen Deficiency Pathologies This example demonstrates that siRNA knockdown of plasminogen does not cause the pathologies associated with complete plasminogen deficiency.

Liver histology images were taken from the liver of mice after treatment with siLuc control or siPlg (siPlg=ms.PLG.1 duplex siRNA of Table 2).

As shown in FIGS. 4A-F liver histology did not show the extensive fibrinous lesions usually observed with Plasminogen deficiency.

Figure 4:
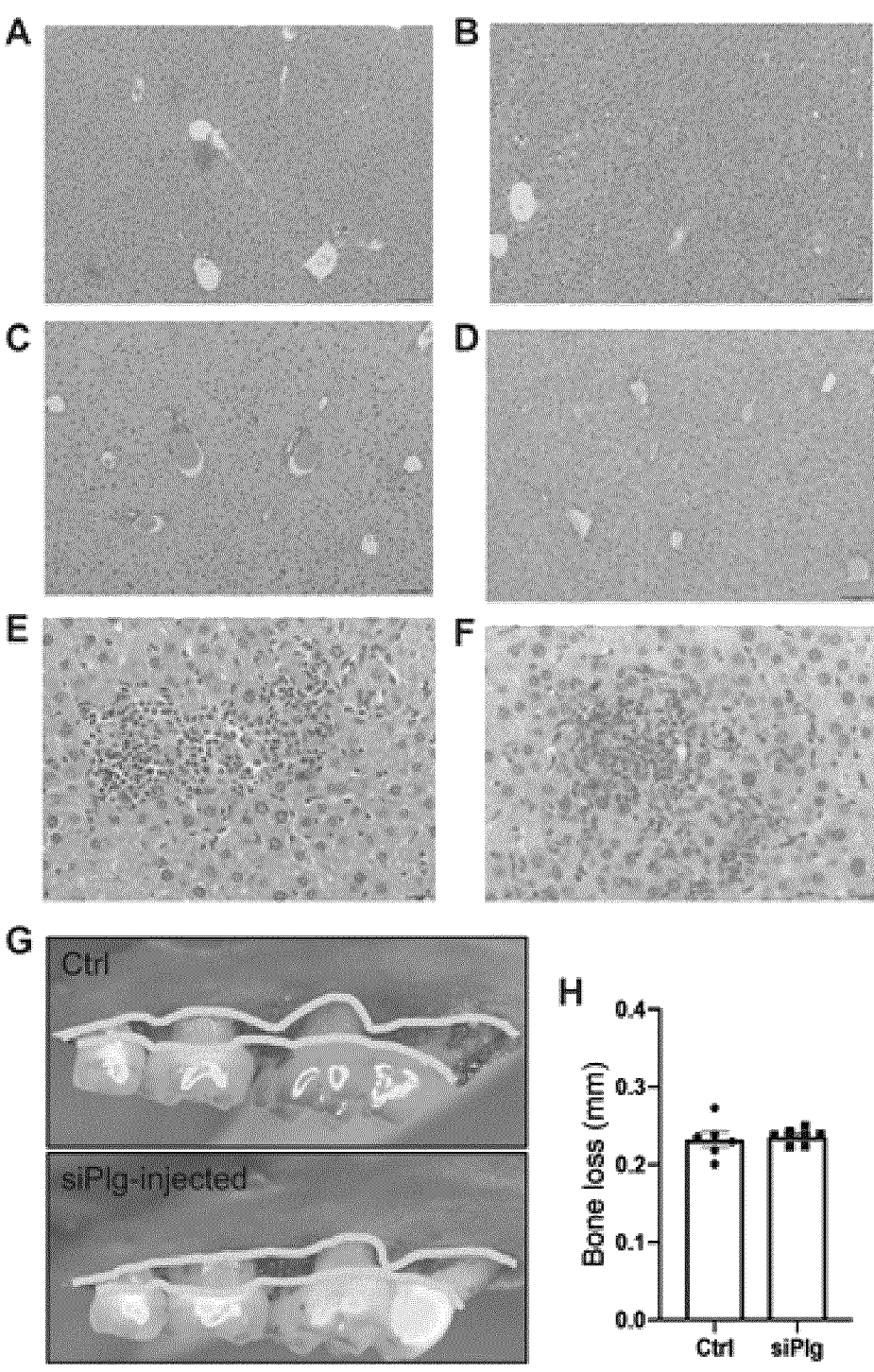
FIGS. 4A and 4B show liver histology images of siLuc, 10×, haematoxylin and eosin stain (H&E stain) (FIG. 4A), representative siPlg, 10×, H&E stain (FIG. 4B) of mice.
FIGS. 4C and 4D show liver histology images of siLuc, 10×, fibrin stain (FIG. 4C), representative siPlg, 10×, fibrin stain (FIG. 4D), of mice.
FIGS. 4E and 4F show liver histology images of small lesion siLuc, 40×, H&E stain (FIG. 4E), small lesion siPlg, 40×, fibrin stain (FIG. 4F).
FIG. 4G shows periodontal bone loss in mice after 12 months of siPlg mediated knockdown. The images show the measured area outlined in the light, thick line.
FIG. 4H shows quantification of bone loss (mm) between mice treated with siPlg and siLuc control measured in the area outlined in FIG. 4G.

Periodontal bone loss, a symptom of Plasminogen deficiency, was also examined in mice. As shown in FIG. 4G and FIG. 4H, periodontal bone loss was not observed after 12 months of siPlg mediated knockdown.

Example 5: Plasminogen Knockdown Stabilizes Clots and Ameliorates Bleeding in Mice This example demonstrates that plasminogen knockdown stabilizes clots against fibrinolysis and ameliorates bleeding in mice with Hemophilia A (F8$^{-/-}$ mice lacking coagulation factor VIII).

The F8$^{-/-}$ mice lacking factor VIII were untreated or treated with siPlg (siPlg=ms.PLG.1 duplex siRNA of Table 2). Wild-type mice were also used as a control in the study.

Figure 5:
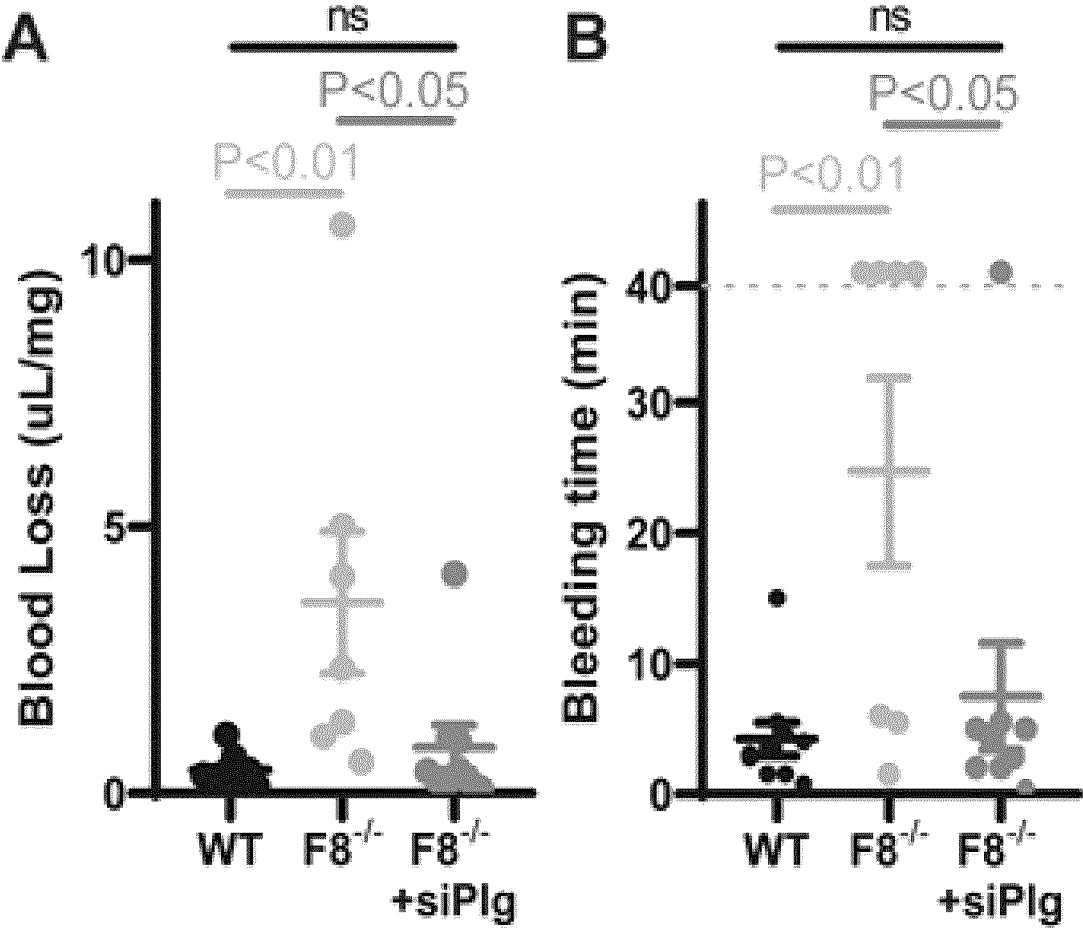
FIG. 5A is a graph showing blood loss (μL/mg) for wild-type mice (WT) and F8$^{-/-}$ mice model of hemophilia (lacking factor VIII) without siPlg (F8$^{-/-}$) and with siPlg (F8$^{-/-}$+siPlg).
FIG. 5B is a graph showing bleeding time (min) for wild-type mice (WT) and F8$^{-/-}$ mice model of hemophilia (lacking factor VIII) without siPlg (F8$^{-/-}$) and with siPlg (F8$^{-/-}$+siPlg).

The results show that siPlg reduced both total blood loss (FIG. 5A), and bleeding time (FIG. 5B) after a saphenous vein puncture model of bleeding in the mouse model of hemophilia A.

Example 6: Plasminogen Knockdown In Vivo in Canines Stabilizes Clots, Ex Vivo This example shows that plasminogen knockdown in vivo in canines stabilizes clots, ex vivo. Additionally, the example shows plasminogen knockdown with siPlg (siPlg=ms.PLG.1 duplex siRNA of Table 2) effectively stabilized clots and decreased bleeding events in two dogs with hemophilia A.

Figure 6:
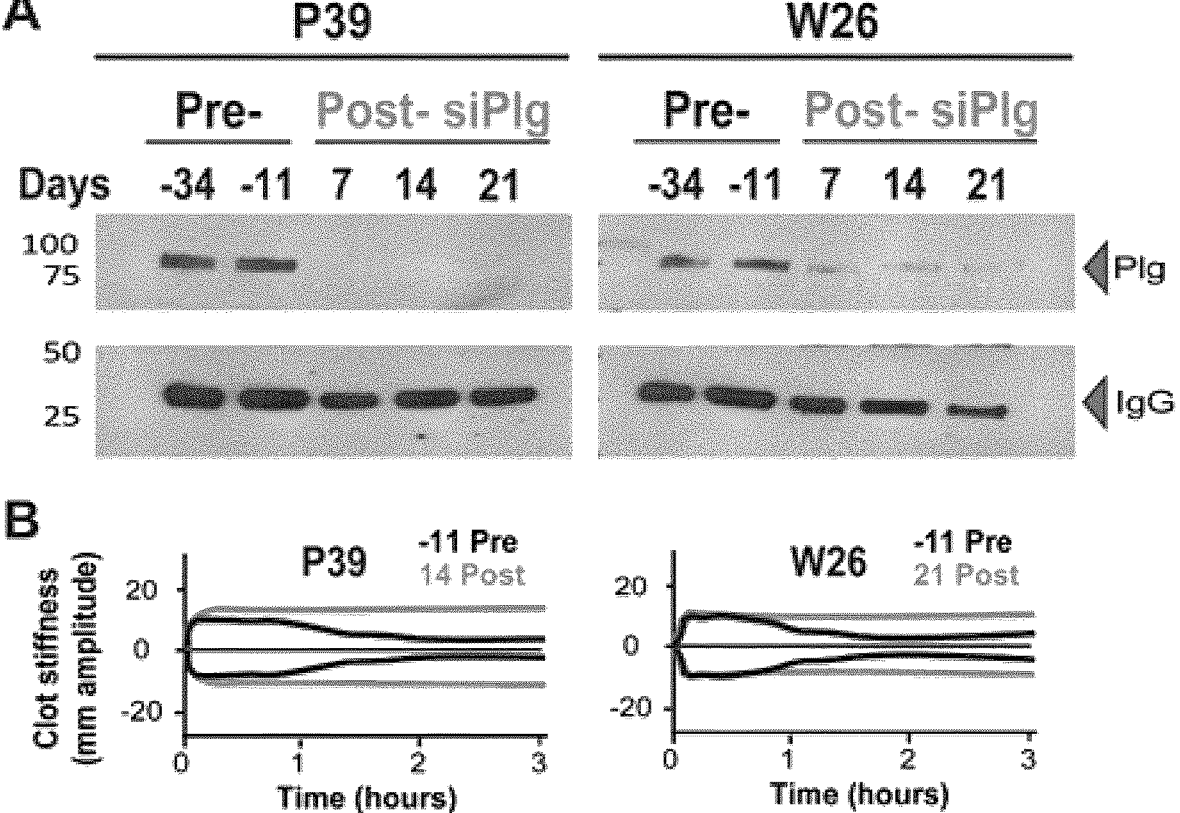
FIG. 6A shows plasminogen knockdown as assessed by western blot after administration of siRNA to two dogs (P39 and W26) having haemophilia. Plasminogen (Plg) and IgG were both assessed by western blot pre- and post-administration of siPlg.
FIG. 6B shows results of thromboelastography (TEG) in amplitude (mm) vs time (hours) to measure clot stiffness in the P39 canine (left graph) and the W26 canine (right graph) pre- and post-treatment as indicated.

The siRNA was administered to two dogs (P39 and W26). Samples were taken pre- and post siPlg treatment to assess plasminogen knockdown by western blot analysis as described in the Materials and Methods. Plasminogen and IgG protein levels were assayed in the western blot analysis. FIG. 6A shows plasminogen knockdown was effective up to 3 weeks after administration of siRNA in the two dogs (P39 and W26). FIG. 6B is a thromboelastography (TEG) demonstrating an increase in plasma clot stability after plasminogen knockdown (lighter line) compared to baseline control (darker black line).

Example 7: Plasminogen Knockdown In Vivo in Canines Stabilized Clots and Decreased Bleeding Events This example shows that plasminogen knockdown with siPlg effectively stabilized clots and decreased bleeding events in two dogs with hemophilia A (HA).

Thromboelastography (TEG) showed increased clot stability in blood from HA dogs treated with siPlg compared to baseline and Tranexamic acid (TXA) treatment.

Figure 7:
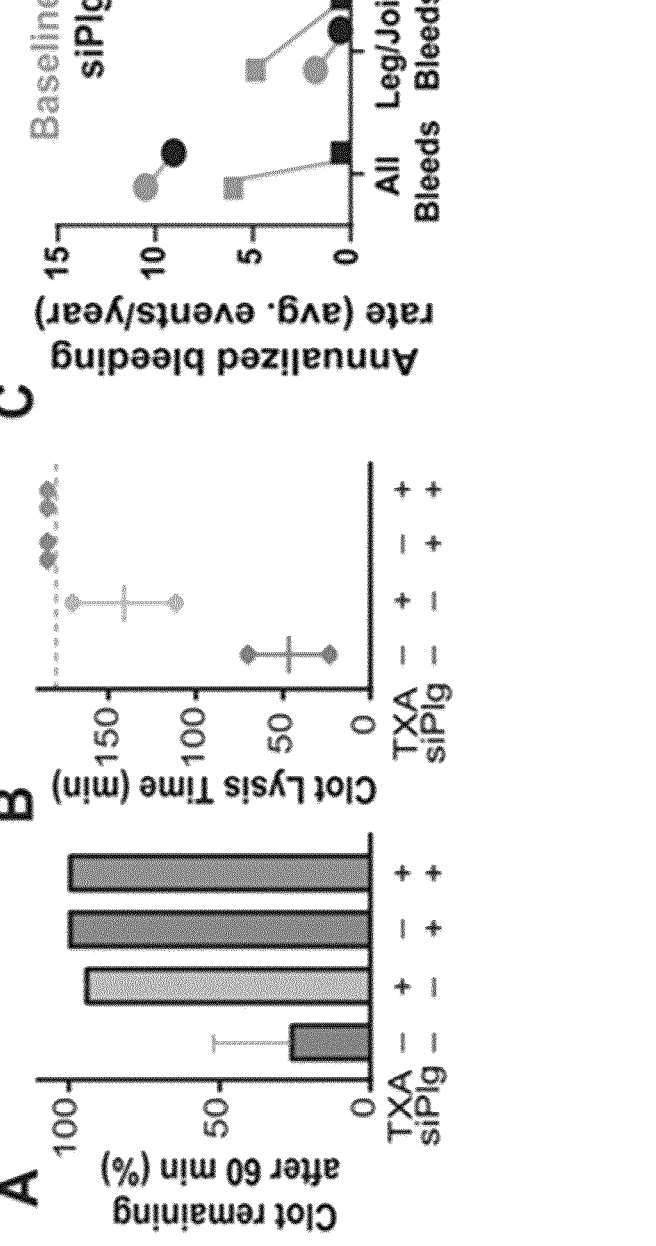
FIG. 7A quantifies clot remaining after 60 min (%) in blood from hemophiliac (HA) dogs treated with siPlg compared to baseline and Tranexamic acid (TXA) treatment. Dogs were treated with neither TXA nor siPlg (leftmost bar), TXA only (left-middle bar), siPlg only (right middle bar), or both TXA and siPlg (right bar).
FIG. 7B quantifies clot lysis time (min) in blood from HA dogs treated with siPlg compared to baseline and Tranexamic acid (TXA) treatment. Dogs were treated with neither TXA nor siPlg (leftmost bar), TXA only (left-middle bar), siPlg only (right middle bar), or both TXA and siPlg (right bar).
FIG. 7C shows annualized bleeding rate (average events per year) from HA dogs before (light tone) and during (black) treatment with siPlg in two dogs (circle, square).

FIG. 7A-C shows plasminogen knockdown with siPlg effectively stabilized clots and decreased bleeding events in two dogs with hemophilia A.

Although the invention has been described and illustrated with reference to the foregoing detailed description and examples, it will be apparent that a variety of modifications and changes may be made without departing from the invention.

---

The invention claimed is:

1. A duplex or single-stranded siRNA molecule against plasminogen mRNA, the siRNA molecule containing modified or unmodified nucleotides and wherein at least one strand of the duplex or the single-stranded siRNA has a sequence that has at least 80% sequence identity to any one of SEQ ID NOs: 1-8 and 15-28.

2. The duplex or single-stranded siRNA molecule of claim 1, wherein the siRNA molecule is 20 to 35 nucleotides in length; or wherein the siRNA molecule is 25 to 35 nucleotides in length.

3. The siRNA molecule of claim 1, wherein at least one strand of the sequence has at least 85% sequence identity to any one of SEQ ID NOs: 1-8 and 15-28;

wherein the sequence has at least 90% sequence identity to any one of SEQ ID NOs: 1-8 and 15-28;

wherein the sequence has at least 95% sequence identity to any one of SEQ ID NOs: 1-8 and 15-28;

wherein the sequence has at least 97% sequence identity to any one of SEQ ID Nos: 1 to 28 NOs: 1-8 and 15-28; or wherein the sequence has at least 98% sequence identity to any one of SEQ ID NOs: 1-8 and 15-28.

4. The siRNA molecule of claim 3, wherein the sequence consists essentially of the sequences of any one of SEQ ID Nos. NOs: 1-8 and 15-28.

5. The siRNA molecule of claim 1, wherein the sequence is a conjugate molecule.

6. The siRNA molecule of claim 5, wherein the conjugate molecule comprises a sugar group.

7. The siRNA molecule of claim 6, wherein the sugar group comprises GalNAc.

8. The siRNA molecule of claim 1, wherein the sequence has at least 80% sequence identity to any one of SEQ ID NOs: 1-8 or 21-28.

9. The duplex or single-stranded siRNA molecule of claim 1, further comprising a lipid nanoparticle.

10. A lipid nanoparticle comprising:

the duplex or single-stranded siRNA molecule of claim 1;

an ionizable, cationic lipid present at between 10 mol % and 85 mol %;

a neutral vesicle-forming lipid selected from at least one of a phospholipid and a triglyceride;

a sterol; and

44 a hydrophilic polymer-lipid conjugate present at between 0.5 mol % and 5 mol %.

11. The siRNA molecule of claim 1 further comprising a pharmaceutically acceptable salt; an excipient; or both.

12. A method of treating a patient having a bleeding disorder comprising administering the siRNA molecule of claim 1 to a patient in need of such treatment thereof.

13. The method of claim 12, wherein the bleeding disorder is selected from one or more of: hemophilia A; hemophilia B; von Willebrand Disease (VWD); a platelet disorder; and menorrhagia.

14. The method of claim 12, wherein the bleeding disorder is hemophilia A or hemophilia B.

15. The method of claim 12, wherein the bleeding disorder is hemophilia A.

16. The method of claim 12, wherein the bleeding disorder is hemophilia B.

17. The method of claim 12, wherein the bleeding disorder is VWD.

18. The method of claim 12, wherein the siRNA molecule stabilizes clots against fibrinolysis; ameliorates bleeding; or both.

19. The lipid nanoparticle of claim 10, further comprising a pharmaceutically acceptable salt; an excipient; or both.

20. An oligonucleotide comprising a contiguous nucleotide sequence of between 10-40, 15-35 or 25-35 nucleotides, wherein the contiguous nucleotide sequence is targeted to hybridize to a sequence selected from the group consisting of SEQ ID NOs: 1-8 or 21-28.

\* \* \* \* \*

```
                        SEQUENCE LISTING

<160> NUMBER OF SEQ ID NOS: 28

<210> SEQ ID NO 1
<211> LENGTH: 25
<212> TYPE: RNA
<213> ORGANISM: Human

<400> SEQUENCE: 1
caagaaguug uccacgcauu uaccu                                    25

<210> SEQ ID NO 2
<211> LENGTH: 27
<212> TYPE: RNA
<213> ORGANISM: Human

<400> SEQUENCE: 2
agguaaaugc guggacaacu ucuuggc                                  27

<210> SEQ ID NO 3
<211> LENGTH: 25
<212> TYPE: RNA
<213> ORGANISM: Human

<400> SEQUENCE: 3
cgcucaugga uacauuccuu ccaaa                                    25

<210> SEQ ID NO 4
<211> LENGTH: 26
<212> TYPE: RNA
<213> ORGANISM: Human

<400> SEQUENCE: 4
uuuggaagga auguauccau gagcgu                                   26

<210> SEQ ID NO 5
<211> LENGTH: 25
<212> TYPE: RNA
<213> ORGANISM: Human

<400> SEQUENCE: 5
guaagcauau cagguuagaa cucuc                                    25

<210> SEQ ID NO 6
<211> LENGTH: 27
<212> TYPE: RNA
<213> ORGANISM: Human

<400> SEQUENCE: 6
gagaguucua accugauaug cuuacuu                                  27
```

-continued

```
<210> SEQ ID NO 7
<211> LENGTH: 25
<212> TYPE: RNA
<213> ORGANISM: Human

<400> SEQUENCE: 7
ugcaaucgcu augaguuucu gaaug                                          25

<210> SEQ ID NO 8
<211> LENGTH: 27
<212> TYPE: RNA
<213> ORGANISM: Human

<400> SEQUENCE: 8
cauucagaaa cucauagcga uugcaca                                        27

<210> SEQ ID NO 9
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (23)..(23)
<223> OTHER INFORMATION: 2'-O-methyladenosine
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(27)
<223> OTHER INFORMATION: gm

<400> SEQUENCE: 9
ucuuuacugu gauauuggaa ugaccug                                        27

<210> SEQ ID NO 10
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: gm
<220> FEATURE:
```

```
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (24)..(24)
<223> OTHER INFORMATION: gm

<400> SEQUENCE: 10
ggucauucca auaucacagu aaaga                                                    25

<210> SEQ ID NO 11
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: gm
<220> FEATURE:
<221> NAME/KEY: modified_base
<222> LOCATION: (27)..(27)
<223> OTHER INFORMATION: gm

<400> SEQUENCE: 11
guaauucauc uucaaguucu ugcuugg                                                  27

<210> SEQ ID NO 12
<211> LENGTH: 25
```

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (24)..(24)
<223> OTHER INFORMATION: 2'-O-methyladenosine

<400> SEQUENCE: 12
aagcaagaac uugaagauga auuac                                              25

<210> SEQ ID NO 13
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
```

```
<223> OTHER INFORMATION: cm
<220> FEATURE:
<221> NAME/KEY: modified_base
<222> LOCATION: (27)..(27)
<223> OTHER INFORMATION: um

<400> SEQUENCE: 13
cucuuuacug ugauauugga augaccu                                                    27

<210> SEQ ID NO 14
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (24)..(24)
<223> OTHER INFORMATION: 2'-O-methyladenosine

<400> SEQUENCE: 14
gucauuccaa uaucacagua aagag                                                      25

<210> SEQ ID NO 15
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
```

-continued

```
<222> LOCATION: (13)..(13)
<223> OTHER INFORMATION: gm
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(27)
<223> OTHER INFORMATION: cm

<400> SEQUENCE: 15
aagcuuuagu aagcagaggu uuugcuc                                                        27

<210> SEQ ID NO 16
<211> LENGTH: 25
<212> TYPE: DNA
<213> ORGANISM: Artificial Sequence Combined DNA/RNA Molecule
<220> FEATURE:
<223> OTHER INFORMATION: Synthetic oligonucleotide - Combined DNA/RNA
      Molecule
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (24)..(24)
<223> OTHER INFORMATION: um

<400> SEQUENCE: 16
gcaaaaccuc ugcuuacuaa agcut                                                          25

<210> SEQ ID NO 17
<211> LENGTH: 27
<212> TYPE: RNA
<213> ORGANISM: Artificial Sequence
<220> FEATURE:
<223> OTHER INFORMATION: Synthetic oligonucleotide
```

-continued

```
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (23)..(23)
<223> OTHER INFORMATION: 2'-O-methyladenosine
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: 2'-O-methyladenosine
<220> FEATURE:
<221> NAME/KEY: modified_base
<222> LOCATION: (27)..(27)
<223> OTHER INFORMATION: gm

<400> SEQUENCE: 17
ucuucacauu caggaauguu gcaguag                                         27

<210> SEQ ID NO 18
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (24)..(24)
```

-continued

```
<223> OTHER INFORMATION: gm

<400> SEQUENCE: 18
acugcaacau uccugaaugu gaaga                                          25

<210> SEQ ID NO 19
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(27)
<223> OTHER INFORMATION: um

<400> SEQUENCE: 19
aggauaaccu uguagaauuc aggucuu                                        27

<210> SEQ ID NO 20
<211> LENGTH: 25
<212> TYPE: DNA
<213> ORGANISM: Artificial Sequence Combined DNA/RNA Molecule
<220> FEATURE:
<223> OTHER INFORMATION: Synthetic oligonucleotide - Combined DNA/RNA
      Molecule
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (12)..(12)
<223> OTHER INFORMATION: um
<220> FEATURE:
```

-continued

```
<221> NAME/KEY: modified_base
<222> LOCATION: (14)..(14)
<223> OTHER INFORMATION: cm
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (24)..(24)
<223> OTHER INFORMATION: cm

<400> SEQUENCE: 20
gaccugaauu cuacaagguu aucct                                              25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide - Combined DNA/RNA
      Molecule
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (24)..(24)
<223> OTHER INFORMATION: cm

<400> SEQUENCE: 21
caagaaguug uccacgcauu uacct                                              25

<210> SEQ ID NO 22
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
```

```
<223> OTHER INFORMATION: gm
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: gm
<220> FEATURE:
<221> NAME/KEY: modified_base
<222> LOCATION: (26)..(26)
<223> OTHER INFORMATION: gm
<220> FEATURE:
<221> NAME/KEY: modified_base
<222> LOCATION: (27)..(27)
<223> OTHER INFORMATION: cm

<400> SEQUENCE: 22
agguaaaugc guggacaacu ucuuggc                                              27

<210> SEQ ID NO 23
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (24)..(24)
<223> OTHER INFORMATION: 2'-O-methyladenosine

<400> SEQUENCE: 23
```

-continued

```
cgcucaugga uacauuccuu ccaaa                                      25

<210> SEQ ID NO 24
<211> LENGTH: 26
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (25)..(25)
<223> OTHER INFORMATION: gm
<220> FEATURE:
<221> NAME/KEY: modified_base
<222> LOCATION: (26)..(26)
<223> OTHER INFORMATION: um

<400> SEQUENCE: 24
uuuggaagga auguauccau gagcgu                                     26

<210> SEQ ID NO 25
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: um
<220> FEATURE:
```

-continued

```
<221> NAME/KEY: modified_base
<222> LOCATION: (18)..(18)
<223> OTHER INFORMATION: gm
<220> FEATURE:
<221> NAME/KEY: modified_base
<222> LOCATION: (24)..(24)
<223> OTHER INFORMATION: um

<400> SEQUENCE: 25
guaagcauau cagguuagaa cucuc                                                    25

<210> SEQ ID NO 26
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(27)
<223> OTHER INFORMATION: um

<400> SEQUENCE: 26
gagaguucua accugauaug cuuacuu                                                  27

<210> SEQ ID NO 27
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: um
```

-continued

```
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (24)..(24)
<223> OTHER INFORMATION: um

<400> SEQUENCE: 27
ugcaaucgcu augaguuucu gaaug                                          25

<210> SEQ ID NO 28
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (25)..(25)
<223> OTHER INFORMATION: 2'-O-methyladenosine
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: 2'-O-methyladenosine

<400> SEQUENCE: 28
cauucagaaa cucauagcga uugcaca                                        27
```